US006331624B1

(12) United States Patent
Koch et al.

(10) Patent No.: US 6,331,624 B1
(45) Date of Patent: Dec. 18, 2001

(54) PROCESS FOR PREPARING 6-AMINOCAPROAMIDE

(75) Inventors: Theodore Augur Koch; Alan Martin Allgeier, both of Wilmington; Mark Jay Harper, Lewes; Sourav Kumar Sengupta, Wilmington, all of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/543,766

(22) Filed: Apr. 5, 2000

(51) Int. Cl.[7] .................................................. C07D 201/02
(52) U.S. Cl. ...................... 540/538; 564/197; 564/198; 540/539
(58) Field of Search .................................. 540/538, 539; 564/197, 198

(56) References Cited

U.S. PATENT DOCUMENTS

| 1,628,190 | 5/1927 | Raney . |
| 3,658,810 | 4/1972 | Tanka et al. . |
| 4,119,655 | 10/1978 | Weitz et al. . |
| 5,302,756 | 4/1994 | McKinney et al. . |
| 5,347,033 | 9/1994 | Witzel et al. . |
| 5,717,089 | * 2/1998 | Wolfers et al. ...................... 540/538 |
| 5,728,556 | 3/1998 | DiCosimo et al. . |
| 5,811,585 | 9/1998 | Dumas et al. . |
| 5,986,126 | 11/1999 | Bunel et al. . |
| 6,005,145 | 12/1999 | Cordier et al. . |

FOREIGN PATENT DOCUMENTS

| 19630788 | 9/1997 | (DE) . |
| 576976 | 1/1994 | (EP) . |
| WO 98/04515 | 2/1998 | (WO) . |
| WO 98/35938 | 2/1998 | (WO) . |

OTHER PUBLICATIONS

Chemische Berichte 92, 2619, 1959.

* cited by examiner

Primary Examiner—Shailendra Kumar

(57) ABSTRACT

A process for the production of 6-aminocaproamide comprising reacting 5-cyanovaleramide with hydrogen in the presence of a metal catalyst. The 6-aminocaproamide is useful, for example, in the production of caprolactam and nylon 6.

21 Claims, No Drawings

PROCESS FOR PREPARING 6-AMINOCAPROAMIDE

BACKGROUND OF THE INVENTION

1. Field of the Invention

The present invention relates to a process for the preparation of 6-aminocaproamide. The 6-aminocaproamide is useful to produce caprolactam, which in turn is useful to produce nylon 6.

2. Description of Related Art

6-Aminocaproamide is a useful intermediate that is suitable for the manufacturing of caprolactam. U.S. Pat. No. 4,119,665 discloses a process for the manufacturing of 6-aminocaproamide by the reaction of ethyl-5-cyanovalerate with ammonia to produce 5-cyanovaleramide, which is then hydrogenated in the presence of ammonia and a supported cobalt and/or nickel catalyst to produce the 6-aminocaproamide. While the process of U.S. Pat. No. 4,199,665 provides good yields of 6-aminocaproamide, it can be hindered by the generation of one mole of ethanol per mole of product. Ethanol handling increases the process costs for waste treatment or recycling. Also, the patent limits the process for the manufacturing of 6-aminocaproamide to the use of a supported cobalt and/or nickel catalyst obtained by a specific process. The catalyst is made by calcining together an appropriate cobalt and/or nickel salt and an $Al_2(OH)_{16}CO_3$ support, thereby forming a solid catalyst which has cobalt and/or nickel distributed throughout it, not just on the surface of the support.

A process for the hydrogenation of cyanocarboxylic acid amides to produce the corresponding aminocarboxylic acid amides in the presence of an unpromoted Raney® nickel catalyst is described in Chemische Berichte 92,2619 (1959). The reaction of the publication occurs in a dioxane solvent and in the presence of ammonia. A process, which provides a higher rate of reaction and avoids the use of the cancer-suspect agent, dioxane, would be desirable.

A process for the preparation of an aqueous mixture of ε-caprolactam and ε-caprolactam precursors, including 6-aminocaproamide is disclosed in published international application WO 9835938. A process that provides a higher yield of 6-aminocaproamide would be desirable from an industrial point of view to simplify purification and provide lower amounts of waste.

SUMMARY OF THE INVENTION

There is a need to improve and overcome deficiencies of the prior processes of preparing 6-aminocaproamide such as the generation of ethanol as a byproduct, a low rate of reaction, the use of dioxane, a complicated reaction, and high amounts of waste.

In accordance with these needs, there is provided according to the present invention a process for the production of 6-aminocaproamide comprising reacting 5-cyanovaleramide with hydrogen in the presence of a metal catalyst selected from supported metal catalysts, sponge metal catalysts, homogenous catalysts, and reduced metal oxide, hydroxide, or carbonate catalysts, wherein if the catalyst is a supported metal catalyst comprising cobalt or nickel, and if the support is calcined, it is calcined before application of the nickel or cobalt.

According to the present invention, there is also provided a process further comprising reacting the 6-aminocaproamide to produce caprolactam, and polymerizing the caprolactam to form a polyamide. Furthermore, there is provided 6-aminocaproamide, caprolactam, and polyamide produced according to the processes of the present invention.

There is also provided a process for the production of 6-aminocaproamide that does not form ethanol, comprising reacting cyanovaleramide with hydrogen in the presence of a metal catalyst.

Further objects, features, and advantages of the invention will become apparent from the detailed description that follows.

DETAILED DESCRIPTION OF THE INVENTION

The present invention provides a process for the production of 6-aminocaproamide by reaction of 5-cyanovaleramide with hydrogen in the presence of a metal catalyst, and optionally in a liquid solvent. 5-Cyanovaleramide may be obtained by processes known in the art. For example, 5-cyanovaleramide may be obtained by reaction of adiponitrile with water in the presence of a supported copper catalyst. See, for example, U.S. Pat. No. 5,347,033, incorporated herein by reference. 5-Cyanovaleramide can also be made by the reaction of cyanovalerate with ammonia in the presence of an alcohol, by ammonolysis of nylon 6,6, and by enzymatic process. See, for example, U.S. Pat. Nos. 5,302,756, 5,728,556, EP 178106B1, and EP 576976 respectively, each incorporated by reference. Unlike U.S. Pat. No. 4,119,665, it is not necessary to produce the 5-cyanovaleramide by a process that results in a by-product alcohol, such as ethanol.

Metal catalysts useful in the present invention can be of many types. The catalyst is used in an amount effective to catalyze the reaction. For example, sponge metal catalysts, homogenous catalysts, reduced metal oxide catalysts, and mixed metal oxide catalysts may be used. Also, supported metal catalysts may be used. The active metal can be selected from, for example, iron, ruthenium, rhodium, iridium, palladium, and platinum. Supported cobalt and nickel catalysts may also be used if they are added to a preformed support material. For example, that is, if the support is to be calcined, in contrast to the process of U.S. Pat. No. 4,119,665, the calcination occurs prior to adding the cobalt or nickel. It is advantageous to first calcine the support, so that the active metal is on the surface of the support, and hence is more readily available to catalyze the reaction. Therefore, there is not much waste of active metal since it is available on the surface for use. Also, if a preformed support is used, there can be better control of particle size. Moreover, it can be economically useful to use a preformed support, since a single support can be used to support numerous active metals.

Any desired sponge metals can be used. A sponge metal has an extended "skeleton" or "sponge-like" structure of metal, with dissolved aluminum and/or silicon and optionally contains promoters. The sponge metal catalysts may also contain surface hydrous oxides, adsorbed hydrous radicals, and hydrogen bubbles in the pores. A description of sponge metal catalysts and their preparation can be found in U.S. Pat. No. 1,628,190, which is incorporated herein by reference.

Preferred sponge metals include nickel, cobalt, iron, ruthenium, rhodium, iridium, palladium, and platinum. The sponge metal may be promoted by one or more promoters selected from the group of Group IA (lithium, sodium, and potassium), IB (copper, silver, and gold), IVB (titanium and zirconium), VB (vanadium), VIB (chromium, molybdenum, and tungsten), VIIB (manganese, rhenium), and VIII (iron, cobalt, nickel, ruthenium, rhodium, palladium, osmium, iridium, and platinum) metals. The promoter can be used in an amount useful to give desired results. For example, the amount of promoter may be any amount less than about 100% by weight of the sponge metal, preferably 0 to about 10% by weight, more preferably 1 to 5% by weight Sponge nickel or sponge cobalt (also known as Raney® catalysts) are particularly suitable as catalysts. Sponge nickel catalysts contain mainly nickel and aluminum, the latter in the form of metallic aluminum, aluminum oxides, or aluminum hydroxides. Small amounts of other metals in elementary or in chemically bound form, such as iron and/or chromium, may be added to the sponge nickel to increase the activity and selectivity for the hydrogenation of certain groups of compounds. As mentioned above, these added metals are usually called promoters, while the catalyst is called promoted sponge nickel. It is particularly preferred to use chromium and/or iron promoted sponge nickel as a catalyst.

Sponge cobalt catalyst also contain aluminum and may contain promoters. Preferred promoters are nickel and chromium, for example, in amounts of about 2% by weight based on the weight of the catalyst.

Examples of sponge metal catalysts that are suitable include the nickel type Degussa-Huls® BLM 112W, W.R. Grace Raney® 2400, and Activated Metals® A-4000. Useful sponge cobalt catalysts include Activated Metals® P8046, Degussa Huls® BLMX 2113Z and W. R. Grace Raney® 2724.

As mentioned above, another useful type of metal catalyst is the supported metal catalysts. A supported metal catalyst is a metal catalyst on a solid support. Any such catalyst may be used in catalytically effective amounts. Preferred metals in the supported metal catalyst include ruthenium, nickel, cobalt, iron, rhodium, iridium, palladium, and platinum. Especially preferred is ruthenium. Preferred solid supports include titanium dioxide, porous aluminum oxide, silicon dioxide, aluminum siliciate, lanthanum oxide, zirconium dioxide, magnesium oxide, zinc oxide, zeolites, and activated charcoal. Particularly preferred solid supports are titanium dioxide, porous aluminum oxide, silicon dioxide, zirconium dioxide, and activated charcoal. Especially useful supported metal catalysts are supported ruthenium catalysts, for example, ruthenium on titanium dioxide. Also, it is acceptable to use a mixture of more than one support and/or more than one catalyst element.

The supported catalysts can be prepared by a variety of ways known in the art. Preferably, a preformed (e.g., already calcined) support is used. For example, if the support material is a solid oxide such as titania, alumina, silica, zirconia and others, the support material would preferably be calcined before application of the metallic component onto the support material. If the metal is cobalt or nickel, the choice of catalyst is preferably those which employ a preformed support material, such as a already calcined oxide.

Any method of placing the catalyst metal on a support can be used. Several methods are known in the art. One method involves applying a solution of salt or oxide to the support, drying the support, and then reducing the salt or oxide. Another method involves applying a salt that is easily thermally decomposed to form a catalytically active species. Suitable salts include nitrate, chloride, acetate, acetyl, acetonate, carboxylate, carbonyl or hydride complexes of one or more of Group IA (lithium, sodium, and potassium), IB (copper, silver, and gold), VIB (chromium, molybdenum, and tungsten), VIIB (manganese, rhenium), and VIII (iron, cobalt, nickel, ruthenium, rhodium, palladium, osmium, iridium, and platinum) elements. Additionally, catalytically active metals can be applied to a support by vapor deposition or by flame spray.

Catalytically active metal is generally applied to the support at about 0.1 to about 90 percent by weight of the total supported catalyst, preferably at about 0.5 to about 50% by weight, more preferably 2 to 25% by weight.

Homogenous catalysts are another useful type of metal catalyst. Homogenous catalysts are soluble metal compounds incorporating one or a combination of a metal such as rhodium, ruthenium, cobalt, nickel, iron, palladium, or platinum, and a hydrocarbon containing ligand which may also contain an atom bonded to the metal atom such as phosphorus, nitrogen, oxygen, carbon, and sulfur.

Another useful type of catalyst is the reduced version of a metal oxide, hydroxide, or carbonate. Such catalysts have an extended skeleton-like metallic structure similar to sponge metal catalysts. However, unlike sponge metal catalysts, these catalysts do not necessarily contain dissolved aluminum or silicon. These catalysts can be prepared by the reduction of bulk metal oxides such as iron oxide or cobalt oxide. The bulk metal oxides may also be prepared as a mixture of metal oxides, or as something other than metal oxides such as carbonates and/or hydroxides optionally mixed with oxides of metals. Preferred oxides, carbonates and/or hydroxides of metals for reduction include one or more of iron, cobalt, nickel, ruthenium, rhodium, palladium, osmium, iridium, platinum, chromium, molybdenum, tungsten, manganese, vanadium, titanium, zirconium, aluminum, silicon, lithium, sodium, potassium, magnesium, calcium, or barium. See WO 98/04515 and U.S. Pat. No. 6,005,145, both incorporated herein by reference.

The reaction of 5-cyanovaleramide with hydrogen can be performed at any desired temperature and pressure. For example, a total pressure of about 100 to about 5000 psi (about 0.7–about 34 MPa), preferably about 300 to about 1500 psi (about 2.1–about 10.3 MPa), more preferably 500 to 1000 psi (3.4–6.8 MPa) can be used. Hydrogen pressure can be about 50 to about 4000 psi (about 0.3–about 28 MPa), preferably about 100 to about 1000 psi, (about 0.7–about 6.8 MPa) more preferably 250 to 750 psi (1.7–5.2 MPa). The molar ratio of hydrogen to 5-cyanovaleramide is typically equal to or greater than about 2:1, preferably about 2:1 to about 200:1, more preferably 2:1 to 100:1.

Reaction temperature can be about 40 to about 220° C., preferably about 70 to about 150° C., more preferably 80 to 120° C.

The reaction is preferably carried out in the absence of air.

Solvents may be used, but are not necessary. Any desired solvent can be used and can be used in an amount to increase the yield of the reaction and/or to remove heat from the reaction. Preferred solvents include ammonia, methanol, water, and mixtures. Most preferred is ammonia. It is also useful to not use a solvent, thereby reducing costs. But, it is likely that the yield without solvent would be reduced.

Typically a mole ratio of about 1:1 to about 100:1 of solvent to 5-cyanovaleramide can be used, preferably about 5:1 to about 40:1, more preferably 10:1 to 20:1. Other solvents, in addition to or in the alternative to the above mentioned solvents, may be used. These include alcohols, esters, hydrocarbons, tetrahydrofuran (THF), dioxane, and ammonium hydroxide. Of these additional solvents, lower alcohols such as methanol and ethanol are preferred. But, unlike some prior art methods, dioxane is not essential in the present method and need not be used.

The reaction of 5-cyanovaleramide with hydrogen may be performed in any type of reactor. For example, a fixed bed reactor in which the hydrogenation catalyst is present can be used. An advantage to the fixed bed reactor is that the separation of reactants and products from the catalyst is simple. Alternatively, the reaction may be carried out in a slurry reactor (such as a batch, a continuously stirred tank reactor, or a bubble column reactor) where the catalyst is present as a slurry during hydrogenation. In this mode the catalyst may be removed by using centrifugal action or filtration.

A wide range of suitable catalyst concentrations may be used. The amount of catalyst is generally dependent on the reactor type. For a fixed bed reactor, the volume per reactor will be high. While with a slurry reactor, the volume will be lower. Typically for a slurry reactor, the catalyst will make up about 0.1 to about 30% by weight of the reactor contents, preferably about 1 to about 15% by weight, more preferably 5 to 10%.

For a fixed bed reactor, the weight hourly space velocity will typically fall in the range about 0.05 to about 100 $hr^{-1}$, preferably about 0.1 to about 10 $hr^{-1}$, more preferably 1.0 to 5 $hr^{-1}$.

The product 6-aminocaproamide may be recovered and purified by a number of methods well known to those skilled in the art. These methods include but are not limited to distillation, extraction and crystallization.

Currently, caprolactam is prepared from phenol in a multi-step process, which generates significant and often undesirable quantities of ammonium sulfate by-product. However, according to the present invention, caprolactam may be synthesized directly from 6-aminocaproamide, thus avoiding the ammonium sulfate by-product. Also, reacting crude, unpurified 6-aminocaproamide produced by the present process simplifies the caprolactam manufacturing process, and avoids the difficult step of purifying 6-aminocaproamide. The resulting caprolactam may then be purified after its synthesis, since caprolactam is much easier to purify than 6-aminocaproamide. 6-Aminocaproamide prepared according to the invention, can be reacted, with or without isolation or purification, to produce caprolactam by methods known in the art, such as reacting it in the presence of one or more solid acid catalysts. Solid acid catalysts include materials that have protons or coordinately unsaturated cationic centers on their surface (*Catalysis of Organic Reactions by Supported Inorganic Reagents* by James H. Clark, VCH Publishers, Inc., N.Y., 1994). Based on the above definition, solid acid catalysts are broadly classified into two catagories namely, Solid Bronstead Acids and Solid Lewis Acids. The former tends to donate a proton while the latter shows the tendency to accept an electron pair (*New Solid Acids* and *Bases Their Catalytic Properties*, by Tanabe, K., Misono, M., Ono, Y., and Hattori, H., Elsevier, 1989). Any desired type of such catalysts can be used. There are different types of solid Bronstead Acids, viz.

1. Simple oxides (silica, alumina, etc.)
2. Mixed oxides (silica-alumina, zeolites, etc.)
3. Natural and synthetic clay minerals (montmorillonite, etc.)
4. Cation exchange resins (perfluoronated sulfonic acid resins, etc.)
5. Supported acids (sulfuric acid-silica, etc.)
6. Solids containing activated water molecules (hydrated sulfates, etc.)

On the other hand, yttrium triflate, aluminum chloride on silica, etc. are some of the examples of solid Lewis acid catalysts.

See U.S. Pat. No. 3,658,810, incorporated herein by reference, for an exemplary process for preparing caprolactam. An example of a particularly useful catalyst is titanium dioxide.

Alternatively, the 6-aminocaproamide can be isolated and purified, and then used to form the caprolactam. The caprolactam can be purified, for example, by extraction, crystallization and/or distillation.

Caprolactam can be used in the manufacturing of synthetic polymers such as polyamides, such as nylon 6. Nylon 6 is formed by ring opening polymerization of the caprolactam using methods known in the art. Caprolactam is also used in textile stiffeners, film coatings, synthetic leather, paint vehicles, cross-linking for polyurethanes, and in the synthesis of lysine.

The invention is illustrated by the following examples that should not be considered limiting.

Unless otherwise indicated, the catalysts used in the examples are commercially available, or were obtained using common methods of making supported catalysts as described in *Catalyst Manufacture* by Koch, T. A., and Stiles, A. B., Dekker, New York, 1995. The 5-cyanovaleramide was prepared by methods known in the art and described in the previously listed patents, incorporated herein by reference in their entirety.

EXAMPLE 1

To a 100 cc Parr Mini Pressure Reactor were added 1.06 g Raney® Ni 2800 slurry (WR Grace) (0.53 g dry weight), 4.0 g water, 20.06 g 5-cyanovaleramide (5-CVAM), and 1.01 g N-methylpyrollidinone (NMP) as internal standard. The reactor was purged with $H_2$ and evacuated. Liquid ammonia (30.0 g) was charged to the reactor, which was heated to 75° C., while being mechanically stirred at 700 rpm. The reactor was pressurized to 900 psig (6.2 MPa) with hydrogen to commence the reaction. After 420 min, gas chromatographic analysis revealed that the reaction had proceeded to 83% conversion of 5-CVAM with 81% yield of 6-aminocaproamide (6-ACAM).

EXAMPLE 2

Example 2 was conducted as Example 1 except that 1.04 g of Raney® Ni promoted with 1–2% Fe and 1–2% Cr (0.52 g dry weight) was used as the catalyst and 20.37 g 5-CVAM was reacted. After 150 min, gas chromatographic analysis revealed that the reaction had proceeded to a 100% conversion of 5-CVAM with a 99% yield of 6-ACAM.

EXAMPLE 3

To a 100 cc Parr Mini Pressure Reactor were added 0.36 g Raney® Ni 2800 slurry (0.18 g dry weight), 3.21 g 5-CVAM, 50 mL dioxane, and 0.165 g NMP as internal standard. The reactor was purged with $H_2$ and vented. Liquid ammonia (4.0 g) was charged to the reactor, which was then heated to 75° C. while being mechanically stirred at 700 rpm. The reactor was pressurized to 900 psig (6.2 MPa) with hydrogen to commence the reaction. After 360 min, gas chromatographic analysis revealed that the reaction had proceeded to 96% conversion of 5-CVAM with a 91% yield of 6-ACAM.

EXAMPLE 4

To a 100 cc Parr Mini Pressure Reactor were added 2.57 g 0.05% Ru 25% Co/alumina (a supported metal catalyst), 10.0 g water, 20.10 g 5-CVAM, and 1.03 g NMP as internal standard. The reactor was purged with $H_2$ and vented. Liquid ammonia (30.0 g) was charged to the reactor, which was then heated to 75° C. while being mechanically stirred at 700 rpm. The reactor was pressurized to 900 (6.2 MPa) psig with hydrogen to commence the reaction. After 125 min, gas chromatographic analysis revealed that the reaction had proceeded to 100% conversion of 5-CVAM with a 99% yield of 6-ACAM.

EXAMPLE 5

To a 100 cc Parr Mini Pressure Reactor were added 1.00 g Raney® Ni promoted with 1–2% Fe and 1–2% Cr (0.50 g dry weight), 4.2 g water, 30.19 g methanol, 20.0 g 5-CVAM, and 1.05 g NMP as internal standard. The reactor was purged with $H_2$, vented and then heated to 75° C. while being mechanically stirred at 700 rpm. The reactor was pressurized to 900 psig (6.2 MPa) with hydrogen to commence the reaction. After 110 min, gas chomatograhic analysis revealed that the reaction had proceeded to 100% conversion of 5-CVAM with a 82% yield of 6-ACAM.

EXAMPLE 6

To a 300 cc Autoclave Engineers Pressure Reactor were added 1.50 g of a slurry of Raney® Co promoted with 2% Ni and 2% Cr (0.75 g dry weight), 10.00 g water, 82.05 g methanol, 30.10 g 5-CVAM, and 1.51 g NMP as internal standard. The reactor was purged with $H_2$. The reactor was sealed under hydrogen at 50 psig and heated to 75° C., while stirring at 150 rpm. Upon reaching this temperature, the reactor was pressurized to 900 psig (6.2 MPa) with hydrogen and the mechanical stirring speed increased to 1000 rpm to commence the reaction. After 140 min, gas chromatographic analysis revealed that the reaction had proceeded to 96% conversion of 5-CVAM with a 82% yield of 6-ACAM.

EXAMPLE 7

Example 6 was repeated except that a slurry of 1.54 g Raney® Co promoted with 2% Ni and 2% Cr (0.77 g dry weight), 1.49 g NMP, 92.00 g water, and no methanol was used. After 40 min, gas chromatographic analysis revealed that the reaction had proceeded to 98% conversion of 5-CVAM with a 74% yield of 6-ACAM.

EXAMPLE 8

To a 100 cc Parr Mini Pressure Reactor were added 2.00 g of a slurry of a catalyst made by the activation of an alloy of 60% Al, 30% Fe, 9% Co, and 1% Ni through treatment with sodium hydroxide to leech out the aluminum (sponge type catalyst, 1.0 g dry weight; this catalyst may be made by the process of U.S. Ser. No. 09/186,839 filed Nov. 5, 1998, incorporated herein by reference), 30.00 g methanol, 10.00 g 5-CVAM, and 0.5 g NMP as internal standard. The reactor was purged with $H_2$ and then vented. The reactor was sealed under hydrogen at 50 psig and then heated to 75° C. while being mechanically stirred at 150 rpm. The reactor was pressurized to 500 psig (3.45 MPa) with hydrogen and mechanical stirring speed increased to 700 rpm to commence the reaction. After 481 min, gas chromatographic analysis revealed that the reaction had proceeded to 87% conversion of 5-CVAM with a 60% yield of 6-ACAM.

EXAMPLE 9

To a 100 cc Parr Mini Pressure Reactor were added 2.56g 15%Co/alumina (a supported metal catalyst), 10.10 g 5-CVAM, 4.0 g water and 0.50 g NMP as internal standard. The reactor was purged with $H_2$ and evacuated. Liquid ammonia (30 g) was charged to the reactor, which was then heated to 75 ° C., while being mechanically stirred at 700 rpm. The reactor was pressurized to 900 psig (6.2 MPa) with hydrogen to commence the reaction. After 390 min, gas chromatographic analysis revealed that the reaction had proceeded to 80% conversion of 5-CVAM with 80% yield of 6-ACAM.

EXAMPLE 10

To a 100 cc Parr Mini Pressure Reactor were added 2.58 g 15%Ni/alumina (a supported metal catalyst), 20.11 g 5-CVAM, 4.0 g water and 0.90 g NMP as internal standard. The reactor was purged with $H_2$ and evacuated. Liquid ammonia (30 g) was charged to the reactor, which was then heated to 75 ° C., while being mechanically stirred at 700 rpm. The reactor was pressurized to 900 psig (6.2 MPa) with hydrogen to commence the reaction. After 390 min, gas chromatographic analysis revealed that the reaction had proceeded to 75% conversion of 5-CVAM with 73% yield of 6-ACAM.

EXAMPLE 11

To a 100 cc Parr Mini Pressure Reactor were added 1.09 g Raney® Ni 2400 slurry (0.55 g dry weight), 25.0 g water, 20.24 g 5-CVAM and 1.01 g NMP as internal standard. The reactor was purged with $H_2$ and evacuated. Liquid ammonia (5.0 g) was charged to the reactor, which was heated to 75° C., while being mechanically stirred at 700 rpm. The reactor was pressurized to 900 psig (6.2 MPa) with hydrogen to commence the reaction. After 90 min, gas chromatographic analysis revealed that the reaction had proceeded to 100% conversion of 5-CVAM with 90% yield of 6-ACAM.

EXAMPLE 12

To a 100 cc Parr Mini Pressure Reactor were added 1.01 g Raney® Ni 2400 slurry (0.51 g dry weight), 4.0 g water, 20.00 g 5-CVAM and 1.00 g NMP as internal standard. The reactor was purged with $H_2$ and evacuated. Liquid ammonia (31.0 g) was charged to the reactor, which was heated to 75° C., while being mechanically stirred at 700 rpm. The reactor was pressurized to 900 psig (6.2 MPa) with hydrogen to commence the reaction. After 100 min, gas chromatographic analysis revealed that the reaction had proceeded to 98% conversion of 5-CVAM with 98% yield of 6-ACAM.

EXAMPLE 13

To a 100 cc Parr Mini Pressure Reactor were added 1.09 g Raney® Co 2724 slurry (0.51 g dry weight), 20.17 g 5-CVAM and 1.01 g NMP as internal standard. The reactor was purged with $H_2$ and evacuated. Liquid ammonia (30.0 g) was charged to the reactor, which was heated to 75° C., while being mechanically stirred at 700 rpm. The reactor was pressurized to 900 psig (6.2 MPa) with hydrogen to commence the reaction. After 210 min, gas chromatographic analysis revealed that the reaction had proceeded to 100% conversion of 5-CVAM with 99% yield of 6-ACAM.

EXAMPLE 14

To a 100 cc Parr Mini Pressure Reactor were added 0.51 g Raney® Ni promoted by 1–2% Fe and 1–2% Cr, 10.02 g 5-CVAM, 10.0 g methanol, and 0.50 g NMP as internal standard. The reactor was purged with $H_2$ and evacuated. Liquid ammonia (30 g) was charged to the reactor, which was then heated to 75° C., while being mechanically stirred at 700 rpm. The reactor was pressurized to 900 psig (6.2 MPa) with hydrogen to commence the reaction. After 323 min, gas chromatographic analysis revealed that the reaction had proceeded to 94% conversion of 5-CVAM with 93% yield of 6-ACAM.

EXAMPLE 15

To a 100 cc Parr Mini Pressure Reactor were added 0.50 g Raney® Co promoted by 2% Ni and 2% Cr, 10.00 g 5-CVAM, 10.0 g methanol and 0.52g NMP as internal standard. The reactor was purged with $H_2$ and evacuated. Liquid ammonia (30 g) was charged to the reactor, which was then heated to 75° C., while being mechanically stirred at 700 rpm. The reactor was pressurized to 900 psig (6.2 MPa) with hydrogen to commence the reaction. After 150 min, gas chromatographic analysis revealed that the reaction had proceeded to 99% conversion of 5-CVAM with 97% yield of 6-ACAM.

EXAMPLE 16

To a 300 cc Autoclave Engineers Stirred Pressure Reactor were added 4.02 g 5%Ru/$TiO_2$ (available from Johnson-Matthey) supported metal catalyst, 10.4 g methanol and 35.08 g 5-CVAM. The reactor was purged with $H_2$ and evacuated. Liquid ammonia (80 g) was charged to the reactor, which was then heated to 110° C., while being mechanically stirred at 1000 rpm. The reactor was pressurized to approximately 1000 psig (6.8 MPa) with hydrogen to commence the reaction. After 12 hr, the reaction was stopped. Gas chromatographic analysis revealed that the reaction had proceeded to 99% conversion of 5-CVAM with 91% yield of 6-ACAM and 4% yield of caprolactam.

Examples 17–19 demonstrate the production of caprolactam using 6-ACAM produced according to the invention.

EXAMPLE 17

6-ACAM made according to Example 13, underwent cylization to form caprolactam (CL). This process was performed in a continuous fixed-bed reactor. The reactor comprised a 0.375" OD×0.305" ID×2.75" long stainless steel tubing, placed in a height-adjustable sand bath. The reaction was carried out in the vapor phase under atmospheric pressure. An ISCO pump (260 ml capacity) was used to feed a 20 wt % solution of 6-ACAM in distilled water (8.0 g of 6-ACAM, 31.6 g of water, and 0.4 g of NMP as an internal standard) into the reactor at the rate of 5 ml/hr. The solution was fed to the reactor via a preheated line followed by a vaporizer. The preheater and the vaporizer were designed to minimize the hold-up time of the reactants in these two sections to prevent polymerization of 6-ACAM. Nitrogen was used as the carrier gas (25 cc/min). The reaction was carried out at a temperature of 325° C. in the absence of a catalyst. The reactor bed was packed with 2 mm diameter inert quartz beads. The product stream containing caprolactam, ammonia, unreacted 6-ACAM, and steam were condensed in two traps. The temperatures of the traps were maintained at a level to ensure complete condensation of the caprolactam, and most of the water and ammonia. The non-condensable carrier gas and some ammonia were vented to the atmosphere. The products were collected at time intervals as shown in Table 1, and analyzed by a Hewlett-Packard Model 5890 gas chromatograph to determine the conversion of 6-ACAM, and the selectivity and yield of CL formed. The conversion, selectivity, and yield as a function of time on stream are reported in Table 1.

EXAMPLE 18

Example 17 was repeated at 300° C. with a 20 wt % solution of 6-ACAM using 1 g of $TiO_2$ catalyst (Degussa AG, Titan Dioxide P25®, No. 7708). The results are shown in Table 2.

EXAMPLE 19

Example 17 was repeated at 325° C. with a 20 wt % solution of 6-ACAM using 1 g of $TiO_2$ (Degussa AG, Titan Dioxide P250, No. 7708) catalyst. The results are shown in Table 3.

TABLE 1

| Time (hr) | Feed Rate (cc/hr) | Conversion (%) | Selectivity (%) | Yield (%) |
| --- | --- | --- | --- | --- |
| 0.0 | 0 | 0.0 | 0.0 | 0.0 |
| 0.9 | 5 | 84.1 | 91.1 | 76.6 |
| 1.9 | 5 | 34.8 | 11.5 | 4.0 |
| 2.9 | 4.8 | 29.4 | 21.0 | 6.2 |
| 3.6 | 4.8 | 51.0 | 34.8 | 17.8 |

TABLE 2

| Time (hr) | Feed Rate (cc/hr) | Conversion (%) | Selectivity (%) | Yield (%) |
| --- | --- | --- | --- | --- |
| 0 | 0 | 0.0 | 0.0 | 0.0 |
| 2 | 5 | 100.0 | 84.4 | 84.4 |
| 3 | 5 | 100.0 | 78.1 | 78.1 |
| 4 | 5 | 100.0 | 75.2 | 75.2 |

TABLE 3

| Time (hr) | Feed Rate (cc/hr) | Conversion (%) | Selectivity (%) | Yield (%) |
| --- | --- | --- | --- | --- |
| 0.0 | 0 | 0.0 | 0.0 | 0.0 |
| 1.0 | 5 | 100.0 | 70.4 | 70.4 |
| 2.3 | 5 | 100.0 | 70.1 | 70.1 |
| 2.9 | 5 | 100.0 | 68.1 | 68.1 |

Those skilled in the art, having the benefit of the teachings of the present invention as hereinabove set forth, can effect numerous modifications thereto. These modifications are to be construed as being encompassed within the scope of the present invention as set forth in the appended claims.

What is claimed:

1. A process for the production of 6-aminocaproamide comprising reacting 5-cyanovaleramide with hydrogen, and in the presence of a metal catalyst selected from supported metal catalysts, sponge metal catalysts, homogeneous catalysts, and reduced metal oxide, hydroxide, or carbonate catalysts, made by reducing a bulk metal oxide, hydroxide, carbonate or mixtures thereof, wherein if the catalyst is a supported metal catalyst comprising cobalt or nickel, and if the support is calcined, it is calcined before application of the nickel or cobalt.

2. A process of claim 1, wherein the metal catalyst is a supported metal catalyst comprising cobalt and/or nickel on a preformed solid support.

3. A process of claim 1, wherein the metal catalyst is a supported metal catalyst comprising ruthenium.

4. A process of claim 3 wherein the metal catalyst is ruthenium supported on titanium dioxide.

5. A process of claim 1, wherein the reacting occurs at a temperature between about 40 to about 220° C.

6. A process of claim 1, wherein the reacting occurs at a pressure between about 0.7–about 34 MPa.

7. A process of claim 1, wherein the metal catalyst is a sponge metal catalyst comprising one or more of nickel, cobalt, iron, ruthenium, rhodium, cobalt, iridium, palladium, and platinum.

8. A process of claim 1, wherein the catalyst is a sponge metal catalyst and the sponge metal catalyst is promoted by at least one promoter.

9. A process of claim 8, wherein the promoter is selected from the group consisting of Group IB, VIB, VIIB, and VIII metals.

10. A process of claim 9, wherein the metal catalyst is a sponge metal catalyst comprising nickel and the promoter comprises one or more of chromium and iron.

11. A process of claim 1, wherein the metal catalyst is a sponge metal catalyst comprising nickel or cobalt.

12. A process of claim 1, wherein the metal catalyst comprises a supported metal catalyst.

13. A process of claim 12, wherein the supported metal catalyst comprises a metal and a solid support, wherein the metal is selected from the group consisting of one or more of nickel, cobalt, iron, ruthenium, rhodium, iridium, palladium, and platinum.

14. A process of claim 1, wherein the supported metal catalyst comprises a metal catalyst and a solid support, wherein the solid support is selected from the group consisting of one or more of titanium dioxide, porous aluminum oxide, silicon dioxide, aluminum silicate, lanthanum oxide, zirconium dioxide, magnesium oxide, zinc oxide, zeolites, and activated charcoal.

15. A process of claim 1, wherein a liquid solvent is present and comprises one or more of ammonia, water, an alcohol, an ester, a hydrocarbon, tetrahdrofuran, dioxane, and ammonium hydroxide.

16. A process of claim 1, further comprising reacting the 6-aminocaproamide to produce caprolactam.

17. A process of claim 16, wherein the 6-aminocaproamide is not purified or isolated.

18. A process of claim 16, further comprising polymerizing the caprolactam to form a polyamide.

19. Polyamide produced according to the process of claim 18.

20. A process for the production of 6-aminocaproamide that does not form ethanol comprising reacting cyanovaleramide with hydrogen in the presence of a metal catalyst.

21. A process of claim 1, wherein the reacting of 5-cyanovaleronitrile with hydrogen is carried out in the absence of dioxane.

* * * * *